United States Patent [19]

Cue, Jr. et al.

[11] Patent Number: 4,751,297
[45] Date of Patent: Jun. 14, 1988

[54] METHOD FOR PREPARATION OF AZETIDINONE-1-OXOACETATE BY OXIDATION OF THE CORRESPONDING 2-HYDROXYACETATE

[75] Inventors: Berkeley W. Cue, Jr., Gales Ferry; Donald K. Pirie, Uncasville, both of Conn.

[73] Assignee: Pfizer Inc., New York, N.Y.

[21] Appl. No.: 28,380

[22] Filed: Mar. 20, 1987

[51] Int. Cl.$^4$ ............... C07F 7/18; C07D 405/12; C07D 409/14; C07B 41/06
[52] U.S. Cl. .................................................. 540/357
[58] Field of Search ........................................ 540/357

[56] References Cited

U.S. PATENT DOCUMENTS 4,155,915  5/1979  Menard et al. ............... 260/306.7
4,619,924  10/1986  Hamanaka ........................ 514/195

OTHER PUBLICATIONS

Sankyo, Chem Abs 98, 143190w (1982).
C. R. Johnson et al., *J. American Chem. Soc.*, 91, 682–687 (1969).
Durst, *Advances in Org. Chem.*, 6, 356–365 (1969).
A. J. Fatiadi, *Synthesis*, 65–104; 133–167 (1976).

*Primary Examiner*—Mark L. Berch
*Attorney, Agent, or Firm*—Peter C. Richardson; Albert E. Frost; Robert K. Blackwood

[57] ABSTRACT

A process for production of a 2-azetidinone-1-oxoacetate of the formula

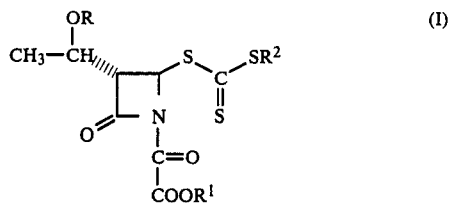

useful as an intermediate for preparation of 2-$SR^2$-substituted-2-penem-3-carboxylate andtibacterial agents;

R is a conventional hydroxy protecting group, $R^1$ is certain carboxy protecting groups and $R^2$ is $(C_1-C_6)$alkyl, $CH_2\overset{(O)_m}{S}CH_3$, $CH_2CH_2\overset{(O)_m}{S}CH_3$ or

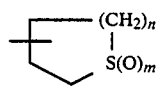

and m and n are each 0, 1 or 2; which comprises contacting a corresponding (2-oxo-1-azetidinyl)-N-2-hydroxyacetate ester of the formula

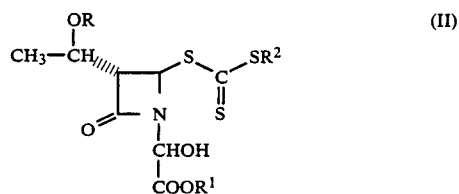

with manganese dioxide.

3 Claims, No Drawings

METHOD FOR PREPARATION OF AZETIDINONE-1-OXOACETATE BY OXIDATION OF THE CORRESPONDING 2-HYDROXYACETATE

BACKGROUND OF THE INVENTION

The invention relates to a novel method for preparation of 2-azetidinone-1-oxoacetate esters of formula (I) by oxidation of the corresponding N-(2-hydroxyacetate) esters of formula (II). The products obtained are valuable intermediates for preparation of antibacterial 2-substituted-2-penems.

Hamanaka, U.S. Pat. No. 4,619,924, which is hereby incorporated herein by reference, discloses antibacterial 2-alkylthiopenem derivatives of the formula

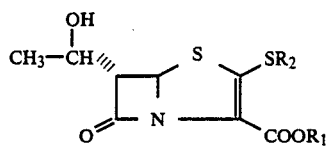

(IV)

wherein $R_1$ is hydrogen or forms an ester group which is hydrolyzed in vivo and values for $R_2$ include $CH_2S(O_m)CH_3$, $CH_2CH_2S(O_m)CH_3$ and

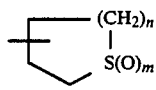

where m and n are each 0, 1 or 2. In a preferred method the penems (IV) were obtained by the following reaction scheme.

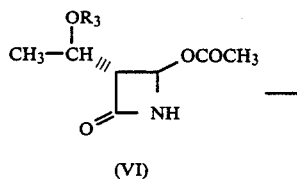

(VI)

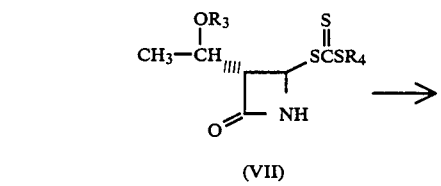

(VII)

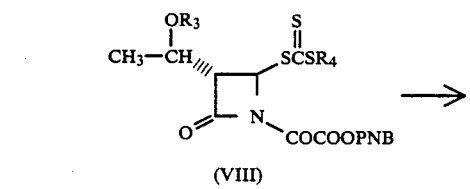

(VIII)

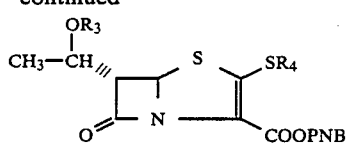

(IX)

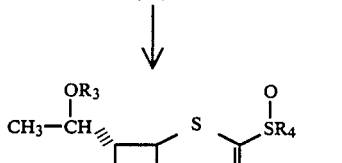

(X)

(X) + $R_2SNa$ ⟶

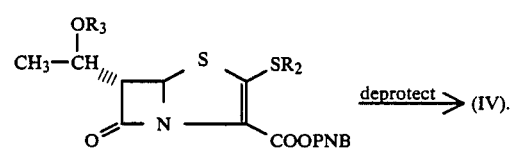

(XI)

$\xrightarrow{\text{deprotect}}$ (IV).

$R_3$ is a silyl hydroxy protecting group, $R_4=(C_1-C_4)$alkyl, PNB=p-nitrobenzyl.

Direct introduction of the desired $SR_2$ group in the first step was not feasible because of side reactions which are known to take place in the conversion of acetidinone (VII) to the oxoacetate ester (VIII). This step is carried out, e.g., by condensation of (VII) with p-nitrobenzyloxalyl chloride in the presence of a tertiary alkylamine, each alkyl having from 1 to 4 carbon atoms, in the presence of reaction-inert solvent, e.g., dichloromethane, at 5°–25° C.

Use of compounds wherein $R_4$ is other than alkyl, such as the above values for $R_2$, above, and those for $R^2$, below, especially the sulfoxides where m=1 gives rise to side reactions such as the Pummerer rearrangement as exemplified below.

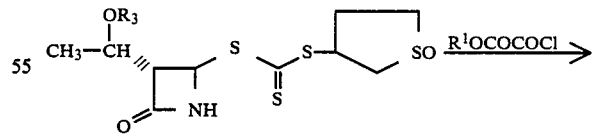

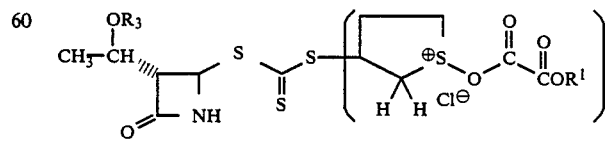

-continued

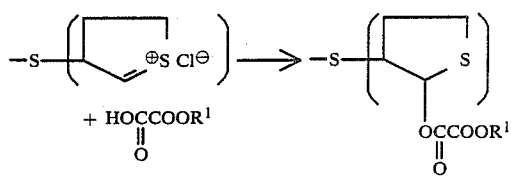

For a review of the Pummerer reaction see, e.g., C. R. Johnson et al., *J. Amer. Chem. Soc.*, 91, 682 (1969) and Durst, *Advances in Organic Chemistry*, 6, 356 (1969).

SUMMARY OF THE INVENTION

The process of the present invention avoids the above undesirable features of the prior art methods by first preparing the azetidinone N-2-hydroxyacetate derivatives of formula (II) by acylation of the appropriate azetidinone (V), below, with a glyoxylic acid ester and oxidation of the hydroxyacetate to the desired oxalamide (I). Thus, the invention is directed to a process for production of a compound of the formula

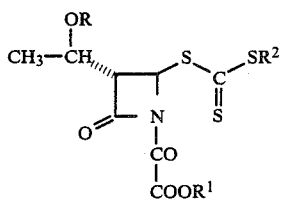 (I)

wherein R is a conventional hydroxy protecting group, $R^1$ is a carboxy protecting group selected from 4-$NO_2C_6H_4CH_2$, $CH_2=CHCH_2$, $CH_2=C(Cl)CH_2$, $(CH_3)_3COOCH_2$, $(CH_3)_3Si$, $(CH_3)_3SiCH_2$, t-$C_4H_9Si(CH_3)_2$, t-$C_4H_9Si(C_6H_5)_2$, or $(CH_3)_2CHCH(CH_3)Si(CH_3)_2$;

$R^2$ is $(C_1$-$C_6)$alkyl, $CH_2SCH_3$, $CH_2CH_2SCH_3$ or

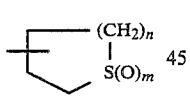

and m and n are independently zero, 1 or 2; which comprises contacting a compound of the formula

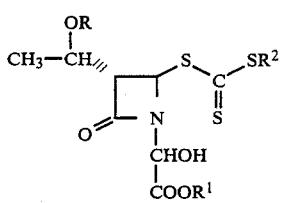 (II)

with manganese dioxide in the presence of a reaction inert organic solvent at a temperature of from 0° to 50° C.

Especially preferred as hydroxy protecting group, R, is a member selected from the group consisting of $(CH_3)_3Si$, $(CH_3)_3SiCH_2$, t-$C_4H_9Si(CH_3)_2$, t-$C_4H_9Si(C_6H_5)_2$, $(CH_3)_2CHCH(CH_3)Si(CH_3)_2$ and 2-tetrahydropyranyl; t-$C_4H_9Si(CH_3)_2$ is most particularly preferred.

A most particularly preferred carboxy protecting group, $R^1$, is 2-chlorallyl.

A particularly preferred value for $R^2$ is

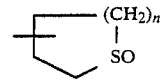

and especially preferred as $R^2$ is

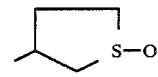

An especially preferred value of m for the invention process is 1.

The compounds of formula (I) provided by the invention process are useful intermediates for preparation of 2-penems of formula (III) which are deprotected to provide antibacterial penems (IV) as disclosed in U.S. Pat. No. 4,619,924.

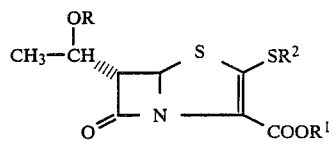 (III)

The present invention further provides novel intermediates of the formula

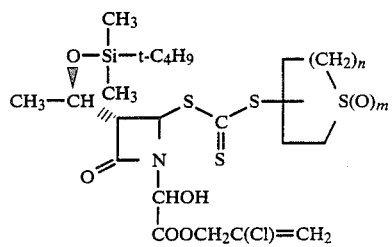 (II')

where m is 1 or 2 and n is zero, 1 or 2. Particularly preferred intermediates of formula (II') are the 3-thiolanyl-1-oxides wherein n and m are each 1.

DETAILED DESCRIPTION OF THE INVENTION

The preparation of the (2-oxo-1-azatidinyl)-2-hydroxyacetate esters of formula (II) is accomplished by methods analogous to those well known in the art; for example, those taught by U.S. Pat. No. 4,155,912 and outlined below.

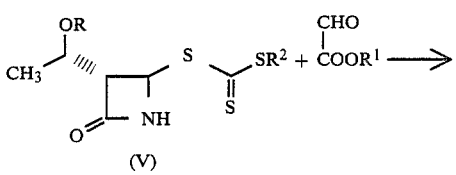
(V)

-continued

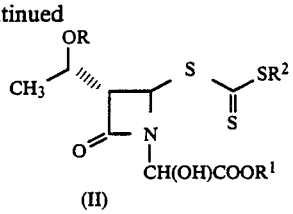

(II)

Typically, equimolar amounts of the appropriate (3S,4R)-3-(1-OR-ethyl)-4-[SR²-(thiocarbonyl)thio]-2-azetidinone (V) and glyoxylic acid ester, or a reactive oxo-derivative thereof such as a hydrate, are reacted in the presence of reaction inert organic solvent, preferably at an elevated temperature to produce the desired intermediate of formula (II) as a mixture of epimers. In a preferred such reaction the solvent employed is benzene and the mixture is maintained at reflux while removing the water formed by the condensation reaction by azeotropic distillation. The product is isolated by removal of solvent. It can be purified and the diastereomers separated, if desired, by chromatographic methods.

The oxidation of the 2-hydroxyacetate ester of formula (II) to the desired (3S,4R)-3-(1-OR-ethyl)-4-[SR²-(thiocarbonyl)thio]-2-azetidinon-1-yl]oxoacetate of formula (I) is preferably carried out employing the mixture of 2-OH epimers (II), described above, by reaction with active manganese dioxide (manganese (IV) oxide) in the presence of reaction inert organic solvent and a catalytic amount of acid. While a wide variety of such solvents, e.g., acetone, methylethyl ketone, acetonitrile, benzene, dimethylformamide and tetrahydrofuran, may be successfully employed in the reaction, acetonitrile is particularly preferred for reasons of economy and efficiency. Examples of suitable acid catalysts for the reaction include sulfuric acid, hydrogen chloride, phosphoric acid, the lower alkylsulfonic acids, benzenesulfonic acid and toluenesulfonic acid. A preferred acid catalyst for the reaction is p-toluenesulfonic acid.

By the term "a catalytic amount" of acid is meant an amount of said acid which is from about 0.01 to 0.5, and especially 0.1–0.3, mole of acid per mole of said starting hydroxy compound of formula (II).

As noted above, the preferred oxidizing agent is active manganese dioxide. A wide variety of methods for preparation of active manganese dioxide are known in the art; see, for example, the extensive review by Fatiadi, Synthesis, 65–104; 133–167 (1976). While many of the active manganese dioxide preparations known in the art will give satisfactory results in the oxidation of the present invention, an especially preferred oxidizing agent is Battery Grade manganese dioxide, for example, Manganese dioxide, Type M which is available from Diamond Shamrock Corporation, Chemetals Division, Cleveland, Ohio 44114.

While only an equimolar amount of manganese dioxide is required by theory, in practice it has been found that use of molar excess of the oxidizing agent is preferred. Thus, a 2 to 30 fold molar excess of manganese dioxide is ordinarily employed, and from 5 to 15 moles manganese dioxide per mole of alcohol of formula (II) is especially preferred.

While the oxidation may be carried out with some success over a rather broad range of temperature, a preferred range is from about 0° to 50° C., and room temperature is especially preferred for convenience, at which temperature the reaction is ordinarily complete in from about 4 to 80 hours.

The desired oxoacetate of formula (I) is then isolated by standard techniques known in the art such as evaporation of solvent, extraction of the residual oil into a water immiscible solvent, e.g., methylene chloride, chloroform or ethyl ether, washing with water and evaporation of solvent. The product thus obtained is often of adequate purity for its intended use as an intermediate for preparation of the corresponding 2-SR substituted-2-penem by cyclization, e.g., by cyclization with triethylphosphite. Alternatively, the product of formula (I) May be purified by standard methods known in the art such as by crystallization or by column chromatography employing, e.g., a silica gel column.

The requisite (3S,4R)-3-(1-OR-ethyl)-4-[SR²-(thiocarbonyl)thio]-2-azetidinones (V) not provided herein are provided in U.S. Pat. No. 4,619,924, which is incorporated herein by reference, by the method outlined below which starts from the well-known methyl 6,6-dibromopenicillanate (XII).

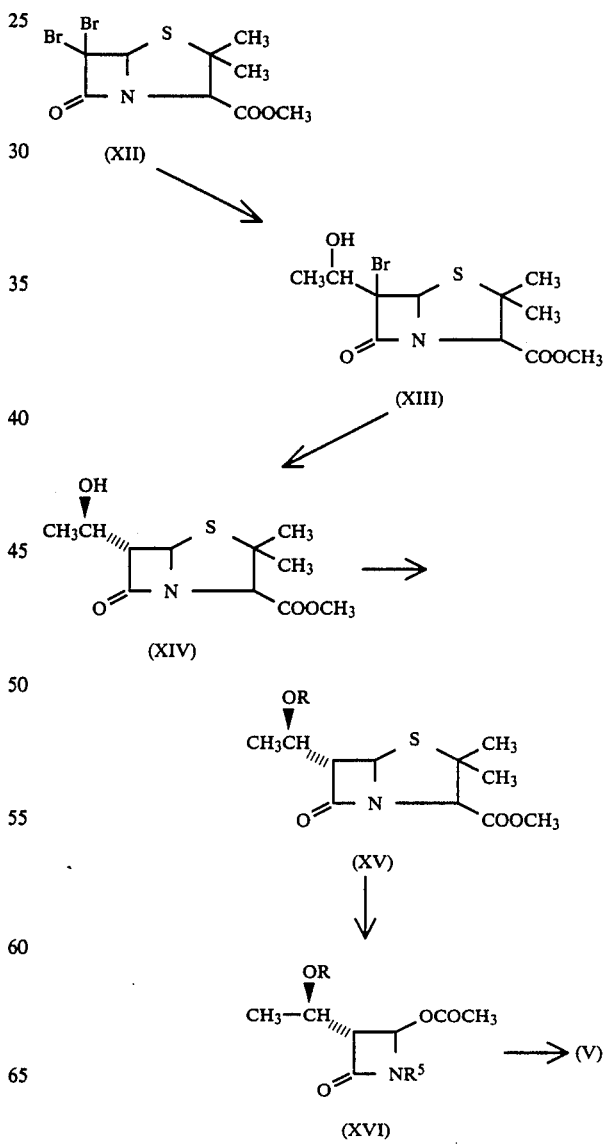

-continued $R^5 =$ H or 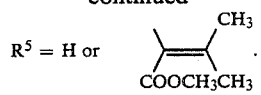

The dibromopenam (XII) undergoes an exchange reaction with t-butylmagnesium chloride at a temperature of from about $-90°$ to $-40°$ C., preferably about $-76°$ C., in a reaction inert solvent such as tetrahydrofuran, ethyl ether or toluene, preferably tetrahydrofuran. The resulting reaction mixture is treated in situ with acetaldehyde at $-80°$ to $-60°$ C., preferably $-76°$ C.

The resulting bromo hydroxypenam (XIII) is hydrogenated to remove the 6-bromo substituent. A suitable hydrogenation catalyst is a noble metal catalyst, e.g., palladium. The reaction is carried out in a protic solvent such as 1:1 water/methanol at a pressure of about 4 atmospheres and at a temperature of from 0° to 30° C., preferably at 25° C.

The resulting alcohol of formula (XIV) can be protected with an hydroxy protecting R, as defined below. Thus, for example, the silyl protecting groups, R, are introduced by reaction of the alcohol of formula (XIV) with the appropriate halosilane, RX, where X is Cl, Br or I. Thus, e.g., dimethyl-t-butylchlorosilane is reacted with the alcohol, (XIV), in the presence of an amine proto acceptor, e.g., imidazole, in a polar, aprotic solvent, such as dimethylformamide, at a temperature of from 5° to 40° C. to form the compound (XV) where R is dimethyl-t-butylsilyl.

The compounds (XV) wherein R is 2-tetrahydropyranyl are prepared from (XIV), typically by reaction with at least an equimolar amount of dihydropyran, in the presence of methylene chloride as solvent and in the presence of pyridinium p-toluenesulfonate as catalyst. The reaction is carried out at or about room temperature for about 4–8 hours. The solvent is evaporated and the product purified by standard extraction methods.

The intermediate compound (XV) is then treated with mercuric acetate in acetic acid at a temperature of about 90° C. to yield the compound (XVI) wherein $R^5$ is 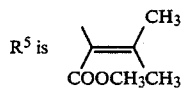

and this is ozonized in the presence of a reaction inert solvent such as dichloromethane at a temperature of from $-80°$ to $-40°$ C., preferably at $-76°$ C. and the reaction product is treated with an alcohol, e.g., methanol to obtain the azetidinone (XVI), $R^5 =$ H.

To obtain the desired compound of formula (V) the azetidinone (XVI), $R^5 =$ H is reacted with the appropriate trithiocarbonate salt of the formula

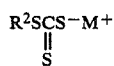

wherein $R^2$ is as defined above for the azetidinone-1-oxoacetates of formula (I), and M is a metal such as sodium or potassium. The reaction is carried out in an organic solvent or water, preferably in a mixture of water and dichloromethane at a temperature of from 0° to 35° C., preferably 25° C.

The above trithiocarbonate salts, $R^2SC(S)S^{-M+}$, are prepared from the appropriate mercaptan $R^2SH$ or by treatment of a thioacetate of formula $R^2SC(O)CH_3$ with an alkali metal alkoxide or oxide, e.g, sodium methoxide or sodium hydroxide, followed by carbon disulfide.

The starting mercaptans of formula $R^2SH$ are provided in U.S. Pat. No. 4,619,924 incorporated herein by reference, or are prepared by methods analogous to those known in the art. For a review see J. L. Wardell, "Preparation of Thiols" in *The Chemistry of the Thiol Group*, S. Patai, editor, John Wiley and Sons, New York, 1974, Chapter 4. See also Volante, *Tetrahedron Letters*, 22, 3119–3122 (1981).

Where $R^2$ groups contain an $S(O)_m$ moiety and n is 1 or 2, they are obtained by oxidation of the corresponding sulfide thioacetate, $R^2SCOCH_3$, by oxidation with an approximately equimolar amount of m-chloroperbenzoic acid to obtain the sulfoxide (n=1) or with 2 moles of oxidant to obtain the sulfone (n=2) without oxidation of the thioacetate sulfur.

EXAMPLE 1

2-Chloroallyl 2-[(3S,4R)-3-(1-t-butyldimethylsilyloxyethyl)-4-(ethylthio[thiocarbonyl]thio)-2-azetidinon-1-yl]-2-hydroxyacetate

[(II), $R=(CH_3)_2Si+$, $R^1=CH_2C(Cl)=CH_2$, $R^2=C_2H_5$]

A benzene (125 ml) solution containing 5.8 g (0.035 mole) 2-chloroallyl glyoxylate hydrate and 14.25 g (0.039 mole) (3S,4R)-3-(1-t-butyldimethylsilyloxyethyl)-4-(ethylthio[thiocarbonyl]thio-2-azetidinone was heated to reflux under a nitrogen atmosphere and maintained at reflux overnight while collecting water in a Dean-Stark trap. The resulting mixture was filtered and the filtrate evaporated to dryness in vacuo. The residue was purified by chromatography on a silica gel column, eluting with 5:1 (v/v) hexane-ethyl acetate. The starting azetidinone is insoluble in the elution solvent and 1.9 g of this starting compound was removed by filtration. The desired product was isolated as a mixture of diastereomers, 10.4 g, a yellow-orange gum. TLC on silica gel plates, 3:1 hexane/ethyl acetate, showed 2 diastereomers, Rf 0.35 and 0.40. IR(CHCl$_3$) showed carbonyl band at 1781 cm$^{-1}$. The diastereomers were separated by rechromatography.

Less Polar isomer: $^1$H-(CDCl$_3$)ppm(delta): 3.97 (d, OH), 4.3 (q, 1H), 4.7 (q, 2H), 5.32 (d, 1H), 6.27 (d, 2H).

More Polar isomer: $^1$H-(CDCl$_3$)ppm(delta): 3.72 (d, OH), 5.25 (d, 1H), 6.19 (d, 2H).

EXAMPLE 2

2-Chloroallyl 2-[(3S,4R)-3-(1-t-butyldimethylsilyloxyethyl)-4-(ethylthio[thiocarbonyl]thio)-2-azetidinon-1-yl]oxoacetate

[(I), $R=(CH_3)_2Si$-$t$-$C_4H_9$, $R^1=CH_2C(Cl)=CH_2$, $R^2=C_2H_5$]

The diastereomeric mixture of alcohols from Example 1, 3.6 g (7.01 mmole), p-toluenesulfonic acid monohydrate (250 mg) and manganese dioxide, Type M*, 9.0 g (0.10 mole) in 100 ml acetonitrile was stirred at room temperature for 66 hours. The mixture was filtered, the filtrate evaporated, the residual oil was dissolved in 100 ml methylene chloride, washed with 50 ml cold water, dried over sodium sulfate, filtered and the filtrate diluted to 250 ml with methylene chloride. This solution was used directly in the next step.

*Available from Chemetals Division, Diamond Shamrock Corporation, Cleveland, Ohio 44114.

EXAMPLE 3

2-Chloroallyl (5R,6S)-6-[(R)-1-t-butyldimethylsilyloxyethyl)-2-(ethylthio-2-penem-3-carboxylate

[(III), R=(CH$_3$)$_2$Si-t-C$_4$H$_9$, R$^1$=CH$_2$C(Cl)=CH$_2$, R$^2$=C$_2$H$_5$]

The methylene chloride solution (250 ml) of 2-chloroallyl (3S,4R)-2-[3-(1-t-butyldimethylsilyloxy)ethyl-4-(ethylthio[thiocarbonyl]thio-2-azetidinon-1-yl]oxoacetate from the previous Example was heated at a gentle reflux and a solution of 2.56 g (15.4 mmole) triethylphosphite in 40 ml methylene chloride was added dropwise over five hours. After the addition was completed, refluxing was continued for 17 hours, the mixture evaporated to a gum and the gum purified by silica gel column chromatography, eluting with 5:1 hexane/ethyl acetate to afford 730 mg of the desired product, m.p. 89°–90° C. TLC-Rf 0.58 3:1 hexane/ethyl acetate. Infrared (CHCl$_3$): 1790 cm$^{-1}$.

$^1$H-NMR(CDCl$_3$ 250 MHz)ppm(delta): 0.88 (s, 9H), 1.27 (d, 3H), 1.38 (t, 3H), 3.7 (q, 1H), 4.24 (m, 1H), 4.76 (q, 2H), 5.37 (d, 1H), 5.65 (q, 2H).

EXAMPLE 4

2-Chloroallyl (3S,4R)-2-[3-((R)-1-t-butyldimethylsilyloxyethyl)-4-(1-oxo-3-thiolanyl[thiocarbonyl]thio)-2-azetidinon-1-yl]-2-hydroxyacetate

[(I), R=(CH$_3$)$_2$Si-t-C$_4$H$_9$, R$^1$=CH$_2$C(Cl)=CH$_2$,

R$^2$ = 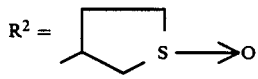

A solution of 3.63 g (8.27 mmole) (3S,4R)-3-((R)-1-t-butyldimethylsilyloxyethyl)-4-(1-oxo-3-thiolanyl[thiocarbonyl]thio)-2-azetidinone and 2.75 g (16.57 mmole) 2-chloroallyl glyoxylate in 100 ml benzene was heated at reflux under a nitrogen atmosphere for 18 hours while removing water in a Dean-Stark trap. The mixture was filtered, solvent evaporated in vacuo and the residue purified by column chromatography on silica gel eluting with 9:1 ethyl acetate/methanol to yield 2.6 g (54%) of the title alcohol. Infrared (CHCl$_3$): 1781 cm$^{-1}$. $^1$H-NMR(CDCl$_3$ 250 MHz) showed the product to be a mixture of 4 isomers.

EXAMPLE 5

2-Chloroallyl 2-[(3S,4R)-3-((R)-1-t-butyldimethylsilyloxyethyl)-4-(1-oxo-3-thiolanyl[thiocarbonyl]thio)-2-azetidinon-1-yl]oxoacetate

[(I), R=(CH$_3$)$_2$Si-t-C$_4$H$_9$, R$^1$=CH$_2$C(Cl)=CH$_2$,

R$^2$ = 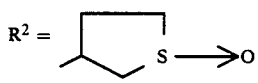

The diastereomeric mixture of alcohols from the previous Example, 2.6 g (4.4 mmole) was combined with 260 mg p-toluenesulfonic acid monohydrate and 5.2 g of Type M manganese dioxide in 150 ml tetrahydrofuran and the mixture stirred at reflux for 19 hours. At this time silica gel TLC of a sample showed a strong product spot at Rf 0.5 in 6:4 methylene chloride/acetone by UV at 254 m, or potassium permanganate spray. The starting alcohol, Rf 0.32. The solvent was evaporated from the reaction mixture, the residue taken up in 150 ml methylene chloride, washed with ice water (100 ml), dried (Na$_2$SO$_4$) and filtered. Evaporation in vacuo gave 2.66 g of gum. The gum was purified by silica gel column chromatography to yield 1.65 g (64%) of the desired diastereomeric ketone. $^1$H-NMR(CDCl$_3$ 250 MHz)ppm(delta): 0.85 (m, 9H), 1.25 (d, 3H), 4.4 (m, 1H), 6.7 (dd, 1H).

EXAMPLE 6

2-Chloroallyl (5R,6S)-6-[(R)-1-t-butyldimethylsilyloxyethyl]-2-(1-oxo-3-thiolanyl)thio-2-penem-3-carboxylate

[(III), R=(CH$_3$)$_2$Si-t-C$_4$H$_9$, R$^1$=CH$_2$C(Cl)=CH$_2$,

R$^2$ = 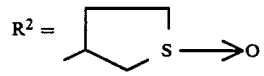

The diastereomeric ketone from the previous Example, 1.65 g (2.82 mmole), was dissolved in ethanol-free chloroform and heated at a gentle reflux. Over a five hour period 0.98 g (5.9 mmole) triethyl phosphite was added dropwise and the resulting mixture refluxed overnight. The solvent was then evaporated and the crude product was purified by silica gel column chromatography, eluting with 6:4 methylene chloride/acetone to afford 720 mg (48%) of product as a waxy solid. Infrared (CHCl$_3$): 1790 cm$^{-1}$. The product is a mixture of two diastereomers.

$^1$H-NMR(CDCl$_3$)ppm(delta): 0.87 (m, 9H), 1.26 (d, 3H), 4.75 (dq, 2H), 5.39 (dd, 1H), 5.66 (m, 2H).

EXAMPLE 7 p-Nitrobenzyl 2-[(3S,4R)-3-(1-t-butyldimethylsilyloxyethyl)-4-(ethylthio[thiocarbonyl]thio)-2-azetidinon-1-yl]-2-hydroxyacetate

[(II), R=(CH$_3$)$_2$Si-t-C$_4$H$_9$, R$^1$=4-NO$_2$CH$_6$H$_4$CH$_2$, R$^2$=C$_2$H$_5$]

A solution of 454 mg (2.0 mmole) 4-nitrobenzyl glyoxylate and 730 mg (2.0 mmole) (3S,4R)-3-(1-t-butyldimethylsilyloxyethyl)-4-(ethylthio[thiocarbonyl]-thio)-2-azetidinone in 30 ml acetonitrile was heated at reflux (nitrogen atmosphere) for 24 hours. Silica gel TLC showed two spots corresponding to the two possible diasteromers (2:1 hexane/ethyl acetate, starting azetidinone has Rf 0.65, product spots at Rf 0.35, 0.38). Evaporation of the reaction mixture gave 1.0 g of crude product which upon column chromatography on silica gel, eluting with 3:1 hexane/ethyl acetate, gave two products.

Less polar diastereomer: $^1$H-NMR(CDCl$_3$)ppm(delta): 1.21 (d, 3H), 6.24 (d, 1H);

More polar diastereomer: $^1$H-NMR(CDCl$_3$)ppm(delta): 1.24 (d, 3H), 6.2 (d, 1H).

EXAMPLE 8 p-Nitrobenzyl 2-[(3S,4R)-3-(R)-(1-t-butyldimethylsilyloxyethyl)-4-(ethylthio[thiocarbonyl]thio)-2-azetidinon-1-yl]oxoacetate

[(I), R=(CH$_3$)$_2$Si-t-C$_4$H$_9$, R$^1$=4-NO$_2$C$_6$H$_4$CH$_2$, R$^2$=C$_2$H$_5$]

To a solution of 100 mg (0.17 mmole) of the azetidine alcohol from the preceding Example in 1.0 ml deuterochloroform was added 100 mg Type M manganese dioxide and the mixture was stirred at room temperature. After 90 minutes another 50 mg increment of manganese dioxide was added, stirring continued for another 90 minutes and the mixture allowed to stand over a 60 hour period. $^1$H-NMR on the filtered reaction mixture showed the required shift of the C-4 hydrogen from 6.2 to 6.9 ppm, indicative of the desired ketone.

EXAMPLE 9

The solution of azetidine oxoacetate obtained above was treated with triethylphosphite (30 microliters, 0.35 mole) by the method of Example 3, eluting the silica gel column with 19:1 toluene/ethyl acetate to yield p-nitrobenzyl (5R,6S)-6-[(R)-1-t-butyldimethylsilyloxyethyl]-2-ethylthio-2-penem-3-carboxylate as a yellow foam.

EXAMPLE 10 t-Butoxycarbonyloxymethyl (3S,4R)-2-[3-(R)-(1-tetrahydropyranyloxyethyl)-4-(methylthiomethylthio[thiocarbonyl]thio)-2-azetidinon-1-yl]-2-hydroxyacetate A. (3S,4R)-2-[3-(R)-(1-Tetrahydropyranyloxyethyl)-4-(methylthiomethylthio[thiocarbonyl]thio)-2-azetidinone To a stirred solution of 2.67 g (10 mmole) 3-(R)-(1-hydroxyethyl)-4-(methylthiomethylthio[thiocarbonyl]thio)-2-azetidinone in 30 ml methylene chloride at room temperature is added 0.8 g pyridinium p-toluenesulfonate and 1.26 g (15 mmole) dihydropyran and the mixture is stirred at 30° C. for five hours. The solvent is evaporated in vacuo, the residual oil is dissolved in ethyl ether, washed with brine, water, dried (Na$_2$SO$_4$) and concentrated in vacuo to afford the title compound. B. A solution of 3.51 g (10 mmole) of the product of Part A, above, and 4.0 g (20 mmole) t-butoxycarbonyloxymethyl glyoxylate in 150 ml benzene is heated at reflux overnight while removing water in a Dean-Stark trap. The resulting product is isolated and purified as described in Example 4 to obtain the desired 2-hydroxyacetate.

EXAMPLE 11

Employing the appropriate azetidinone of formula

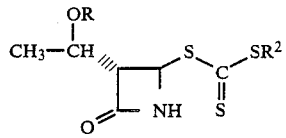

and the appropriate glyoxalate ester CHOCOOR$^1$ in the procedure of Example 1, 4 or 10 affords the corresponding hydroxyacetate compound of the formula

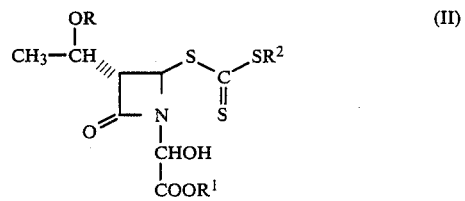

wherein R, R$^1$ and R$^2$ are as defined below.

| R | R$^1$ | R$^2$ |
|---|---|---|
| (C$_6$H$_5$)$_2$Si(t-C$_4$H$_9$) | CH$_2$CH=CH$_2$ | CH$_2$SOCH$_3$ |
| (CH$_3$)$_3$Si | (CH$_3$)$_3$Si | CH$_2$CH$_2$SOCH$_3$ |
| (CH$_3$)$_3$SiCH$_2$ | (CH$_3$)$_3$SiCH$_2$ | n-C$_6$H$_{13}$ |
| (CH$_3$)$_2$Si(t-C$_4$H$_9$) | 4-NO$_2$C$_6$H$_4$CH$_2$ | i-C$_4$H$_9$ |
| (CH$_3$)$_2$CHCH(CH$_3$)Si(CH$_3$)$_2$ | CH$_2$=C(Cl)CH$_2$ | n-C$_4$H$_9$ |
| (CH$_3$)$_3$Si | (CH$_3$)$_3$SiCH$_2$ | CH$_2$SO$_2$CH$_3$ |
| (CH$_3$)$_2$Si(t-C$_4$H$_9$) | (CH$_3$)$_2$Si(t-C$_4$H$_9$) | CH$_2$CH$_2$SCH$_3$ |
| (CH$_3$)$_2$Si(t-C$_4$H$_9$) | (C$_6$H$_5$)$_2$Si(t-C$_4$H$_9$) | CH$_2$CH$_2$SO$_2$CH$_3$ |
| (CH$_3$)$_2$Si(t-C$_4$H$_9$) | (CH$_3$)$_2$CHCH(CH$_3$)Si(CH$_3$)$_2$ | C$_2$H$_5$ |
| (CH$_3$)$_2$Si(t-C$_4$H$_9$) | CH$_2$=C(Cl)CH$_2$ | 1-oxothietan-3-yl |
| 2-tetrahydropyranyl | CH$_2$=C(Cl)CH$_2$ | 1,1-dioxo-3-thiolanyl |
| 2-tetrahydropyranyl | CH$_2$=C(Cl)CH$_2$ | 3-thianyl |
| (CH$_3$)$_2$Si(t-C$_4$H$_9$) | CH$_2$=C(Cl)CH$_2$ | 4-thianyl |

EXAMPLE 12

Oxidation of the products of the preceding Example with active manganese dioxide by the method of Examples 2 or 5 affords the corresponding 2-oxoacetate compounds of the formula

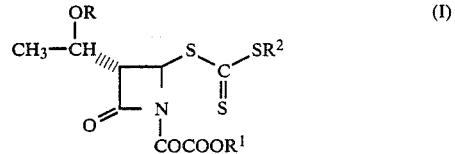

in like manner, where R, R$^1$ and R$^2$ are as defined in Example 11.

PREPARATION A

2-Chloroallyl Tartarate

D-Tartaric acid (1 mole), 2-chloroallyl alcohol (2 moles) and a catalytic amount of p-toluenesulfonic acid monohydrate were combined in toluene and the mixture was heated at reflux for four days while removing water by azeotropic distillation. The resulting mixture was cooled, washed with water, the aqueous layers extracted with ethyl acetate. The combined organic layers were dried (Na$_2$SO$_4$) and solvent evaporated in vacuo. The last traces of toluene were removed by azeotropic distillation with ethanol. Yield, 60% of theory.

$^1$H-NMR(CDCl$_3$)ppm(delta): 3.67 (s, OH), 4.7 (s, 1H), 4.82 (s, 2H), 5.5 (dd, 2H).

PREPARATION B

2-Chloroallyl Glyoxalate Hydrate

To a solution of 6.3 g (0.021 mole) 2-chloroallyl tartarate in 300 ml ethyl ether was added 5.02 g (0.022 mole) periodic acid and the mixture was stirred for two hours at room temperature. The mixture was filtered and the filtrate evaporated to afford 5.83 g (83%) of the title compound.

$^1$H-NMR(CDCl$_3$)ppm(delta) shows loss of CHOH at 4.7 ppm which is characteristic of tartaric acid.

What is claimed is:

1. A compound of the formula

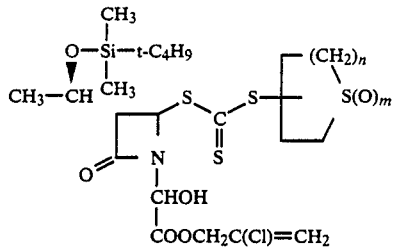

where m is 1 or 2 and n is zero, 1 or 2.

2. A compound according to claim 1 wherein m is 1 and n is 1 or 2.

3. A compound according to claim 2 of the formula

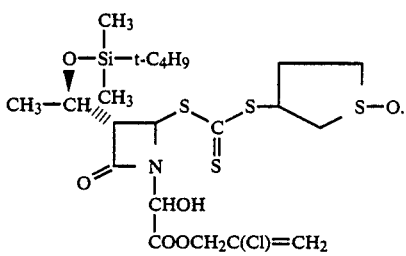

* * * * *